United States Patent
Li et al.

(10) Patent No.: US 10,815,231 B2
(45) Date of Patent: Oct. 27, 2020

(54) [1,2,4] TRIAZOLO [1,5-A] PYRIDINE DERIVATIVE AND CRYSTALLINE FORM THEREOF

(71) Applicant: WEST CHINA HOSPITAL, SICHUAN UNIVERSITY, Chengdu, Sichuan (CN)

(72) Inventors: Weimin Li, Sichuan (CN); Yang He, Sichuan (CN); Li Zhang, Sichuan (CN); Bojiang Chen, Sichuan (CN); Zhixin Qiu, Sichuan (CN)

(73) Assignee: WEST CHINA HOSPITAL, SICHUAN UNIVERSITY, Chengdu, Sichuan (CN)

( * ) Notice: Subject to any disclaimer, the term of this patent is extended or adjusted under 35 U.S.C. 154(b) by 0 days.

(21) Appl. No.: 16/314,329

(22) PCT Filed: Aug. 16, 2016

(86) PCT No.: PCT/CN2016/095503
§ 371 (c)(1),
(2) Date: Dec. 28, 2018

(87) PCT Pub. No.: WO2018/000549
PCT Pub. Date: Jan. 4, 2018

(65) Prior Publication Data
US 2019/0337937 A1 Nov. 7, 2019

(30) Foreign Application Priority Data

Jun. 29, 2016 (CN) .......................... 2016 1 0496719
Jun. 29, 2016 (CN) .......................... 2016 1 0514454

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01); *C07B 2200/13* (2013.01)

(58) Field of Classification Search
CPC ........................................... C07D 471/04
USPC .......................................... 546/119
See application file for complete search history.

(56) References Cited

FOREIGN PATENT DOCUMENTS

| CN | 101535307 A | 9/2009 | |
|---|---|---|---|
| CN | 102131390 A | 7/2011 | |
| CN | 102203093 A | 9/2011 | |
| WO | 2008065198 A1 | 6/2008 | |
| WO | WO 2009047514 | * 4/2009 | |
| WO | WO 2009155565 | * 12/2009 | ............. A01N 43/64 |

OTHER PUBLICATIONS

West, Solid State Chemistry and Its Applications, john Wiley & Sons, 1984.*

* cited by examiner

*Primary Examiner* — Nizal S Chandrakumar
(74) *Attorney, Agent, or Firm* — Novick, Kim & Lee, PLLC; Allen Xue (57) ABSTRACT

The present invention discloses [1,2,4]triazolo[1,5-a]pyridine derivatives, as well as the crystalline form thereof. Compounds provided in the present invention have significant inhibitory effects on tumor cells, can be used for the prevention and/or treatment of tumor-related diseases, especially lung cancer, and have wide application prospects.

(I)

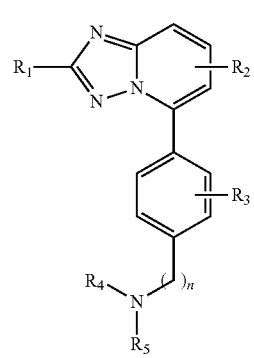

2 Claims, 2 Drawing Sheets

[1,2,4] TRIAZOLO [1,5-A] PYRIDINE DERIVATIVE AND CRYSTALLINE FORM THEREOF

TECHNICAL FIELD

The present invention relates to [1,2,4]triazolo[1,5-a]pyridine derivatives and crystals thereof.

BACKGROUND ART

At present, lung cancer is one of the malignant tumors with the fastest growth of morbidity and mortality, as well as the largest threat to population health and life.

However, although there are many kinds of drugs for the treatment of lung cancer on the market, all of them have various defects, such as low bioavailability, bad specificity, great toxic and side effect and so on. While these shortcomings are often due to the structural features of compounds themselves and their targets, that are difficult to overcome in the further study.

Therefore, the persons in this field all hope to synthesize various compounds with different structures, as well as various crystals thereof, to explore the new targets and overcome above shortcomings.

CONTENT OF INVENTION

In order to solve above problems, the present invention provides [1,2,4]triazolo[1,5-a]pyridine derivatives with novel structures.

The present invention provides compounds of formula (I), or the pharmaceutically acceptable salts thereof, or the solvates thereof:

(I)

In which,
$R_1$ represents halogens, —CN, —OH, —NH$_2$, —NH(C$_1$-C$_4$ alkyl) or —N(C$_1$-C$_4$ alkyl)$_2$;
$R_2$ and $R_3$ independently represent none, or one or more halogens, or one or more C$_1$-C$_4$ alkyls in the ring of their linkage, respectively;
$R_4$ and $R_5$ independently represent hydrogen, halogen or C$_1$-C$_4$ alkyl, respectively; or, $R_4$ and $R_5$, together with the nitrogen linked with them, form 5-7 members heterocyclic ring containing 0-1 oxygen or sulfur atom, in which the carbons can be optionally further substituted by C$_1$-C$_4$ alkyl;
n represents 1, 2, or 3.
Further, $R_1$ represents Cl, Br, I, —CN, or —NH$_2$.
Further, $R_2$ and $R_3$ represent none.

Further, $R_4$ and $R_5$, together with the nitrogen linked with them, form 5-7 members heterocyclic ring containing 0-1 oxygen.

Further, said heterocyclic ring is a morpholine ring.

Further, n is 1.

Further, the compounds are one of the following compounds:

The present invention provides a method for the preparation of compounds of formula (I), that includes the following steps:

(Ia)

(Ib)

In which, R₁ represents Cl, Br, or I; $R_2$-$R_5$ are the same as those defined in claim 1, and $R_4$ and $R_5$ can not simultaneously be hydrogen;

Using compounds of formula (Ia) as starting material, compounds of formula (Ib) is prepared by the diazotization reaction of amino group and the halogenated reaction;

or, (Ic)

(Id)

$R_1$ represents cyano, and $R_2$-$R_5$ are the same as those defined in claim 1, Using compounds of formula (Ic) as starting material, compounds of formula (Id) is prepared by reacting with CuCN.

The present invention provides the uses of compounds, or solvates thereof, or pharmaceutically acceptable salts thereof in the preparation of JAK kinase inhibitory drugs.

The present invention provides the uses of compounds, or solvates thereof, or pharmaceutically acceptable salts thereof in the preparation of anti-tumor drugs.

Further, said drugs are those for the treatment of lung cancer.

Further, said lung cancer is non-small-cell lung carcinoma.

The present invention provides a new crystal form of [1,2,4]triazolo[1,5-a]pyridine derivative with novel structure.

The present invention provides the crystal form A of compound of formula (III), (III)

In the X-ray powder diffraction of this crystal form, the typical peaks are observed at 2θ diffraction angles of 9.85±0.20, 10.13±0.20, 17.19±0.20, 17.48±0.20, 17.56±0.20, 17.64±0.20, 17.72±0.20, 19.36±0.20, 19.80±0.20, 19.97±0.20, 20.16±0.20, 20.22±0.20, 20.86±0.20, 21.01±0.20, 21.26±0.20, 23.84±0.20, 23.92±0.20, 24.43±0.20, 26.23±0.20, 27.55±0.20, and 27.64±0.20.

Further, in the X-ray powder diffraction of this crystal form, the typical peaks are observed at 2θ diffraction angles of 8.54±0.20, 9.85±0.20, 10.13±0.20, 13.55±0.20, 13.80±0.20, 14.50±0.20, 15.32±0.20, 16.32±0.20, 17.19±0.20, 17.48±0.20, 17.56±0.20, 17.64±0.20, 17.72±0.20, 19.36±0.20, 19.80±0.20, 19.97±0.20, 20.16±0.20, 20.22±0.20, 20.86±0.20, 21.01±0.20, 21.26±0.20, 23.84±0.20, 23.92±0.20, 24.43±0.20, 24.86±0.20, 26.23±0.20, 27.06±0.20, 27.37±0.20, 27.55±0.20, 27.64±0.20, 28.31±0.20, 28.46±0.20, 29.60±0.20, 30.45±0.20, 30.70±0.20, 31.62±0.20, 32.70±0.20, 33.49±0.20, 34.12±0.20, 35.97±0.20, 37.17±0.20, 37.74±0.20, 38.16±0.20, 38.94±0.20, 39.28±0.20, 40.18±0.20, 40.86±0.20, 41.58±0.20, 43.07±0.20, 43.61±0.20, 44.98±0.20, 45.26±0.20, 48.21±0.20, 49.27±0.20, 50.99±0.20, 52.79±0.20, and 53.56±0.20.

Further, in the X-ray powder diffraction of this crystal form, the relative intensity for typical peaks at above 2θ diffraction angles is:

| 2θ values (°) | Relative intensity (%) |
|---|---|
| 8.54 ± 0.20 | 1.65 |
| 9.85 ± 0.20 | 11.91 |
| 10.13 ± 0.20 | 15.05 |
| 13.55 ± 0.20 | 8.38 |
| 13.80 ± 0.20 | 4.86 |
| 14.50 ± 0.20 | 5.56 |
| 15.32 ± 0.20 | 4.47 |
| 16.32 ± 0.20 | 9.74 |
| 17.19 ± 0.20 | 16.07 |
| 17.48 ± 0.20 | 70.83 |
| 17.56 ± 0.20 | 92.31 |
| 17.64 ± 0.20 | 100.00 |
| 17.72 ± 0.20 | 64.71 |
| 19.36 ± 0.20 | 10.91 |
| 19.80 ± 0.20 | 9.94 |
| 19.97 ± 0.20 | 14.45 |
| 20.16 ± 0.20 | 22.79 |
| 20.22 ± 0.20 | 23.28 |
| 20.86 ± 0.20 | 26.93 |
| 21.01 ± 0.20 | 30.46 |
| 21.26 ± 0.20 | 10.20 |
| 23.84 ± 0.20 | 25.32 |
| 23.92 ± 0.20 | 25.23 |
| 24.43 ± 0.20 | 15.02 |
| 24.86 ± 0.20 | 3.55 |
| 26.23 ± 0.20 | 11.11 |
| 27.06 ± 0.20 | 4.45 |
| 27.37 ± 0.20 | 8.99 |
| 27.55 ± 0.20 | 17.59 |
| 27.64 ± 0.20 | 17.04 |
| 28.31 ± 0.20 | 6.28 |
| 28.46 ± 0.20 | 5.87 |
| 29.60 ± 0.20 | 2.00 |
| 30.45 ± 0.20 | 3.12 |
| 30.70 ± 0.20 | 3.30 |
| 31.62 ± 0.20 | 5.06 |
| 32.70 ± 0.20 | 3.09 |
| 33.49 ± 0.20 | 0.85 |
| 34.12 ± 0.20 | 0.80 |
| 35.97 ± 0.20 | 0.69 |
| 37.17 ± 0.20 | 0.80 |
| 37.74 ± 0.20 | 0.79 |
| 38.16 ± 0.20 | 0.44 |
| 38.94 ± 0.20 | 1.28 |
| 39.28 ± 0.20 | 1.03 |
| 40.18 ± 0.20 | 3.08 |
| 40.86 ± 0.20 | 0.64 |
| 41.58 ± 0.20 | 0.62 |
| 43.07 ± 0.20 | 1.70 |
| 43.61 ± 0.20 | 1.57 |
| 44.98 ± 0.20 | 1.96 |
| 45.26 ± 0.20 | 1.99 |
| 48.21 ± 0.20 | 0.48 |
| 49.27 ± 0.20 | 1.10 |
| 50.99 ± 0.20 | 0.73 |
| 52.79 ± 0.20 | 0.51 |
| 53.56 ± 0.20 | 0.76 |

Figure 1:
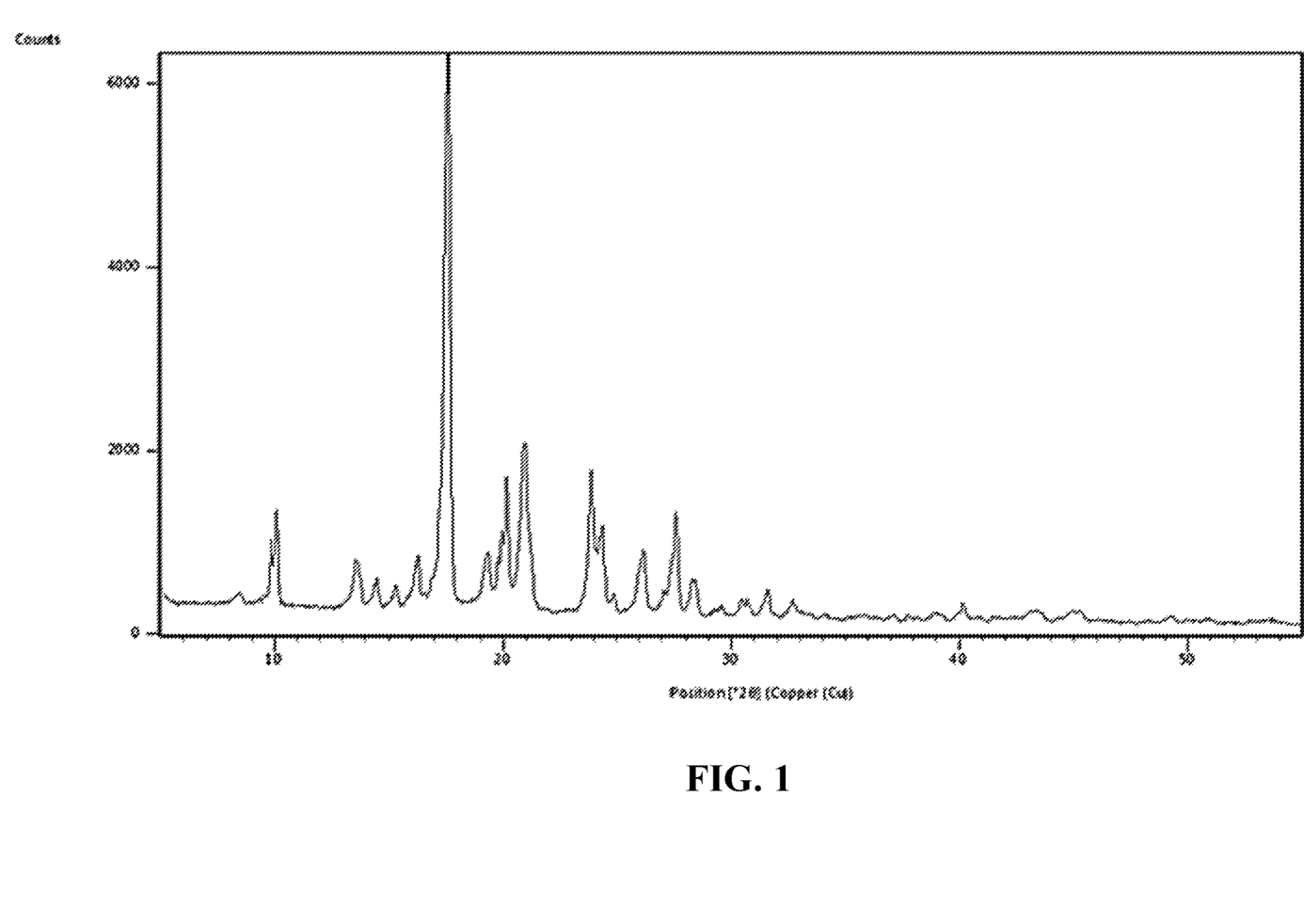
FIG. 1 is the X-ray powder diffraction pattern of crystal form A according to the present invention, using Cu-Ka irradiation.

Further, this crystal form has the X-ray powder diffraction pattern, basically as shown in FIG. 1. The present invention also provides crystal form B of compound of formula (IV), (IV)

In the X-ray powder diffraction of this crystal form, the typical peaks are observed at 2θ diffraction angles of 9.80±0.20, 14.93±0.20, 19.39±0.20, 19.78±0.20, 22.95±0.20, 29.90±0.20, 30.20±0.20, 30.29±0.20, 38.03±0.20, 38.14±0.20, 46.06±0.20, 46.19±0.20, 54.34±0.20, and 54.48±0.20. Further, in the X-ray powder diffraction of this crystal form, the typical peaks are observed at 2θ diffraction angles of 9.80±0.20, 10.57±0.20, 13.79±0.20, 14.93±0.20, 15.85±0.20, 17.63±0.20, 17.96±0.20, 18.27±0.20, 19.16±0.20, 19.39±0.20, 19.60±0.20, 19.78±0.20, 22.03±0.20, 22.95±0.20, 23.62±0.20, 24.92±0.20, 25.47±0.20, 26.82±0.20, 26.98±0.20, 27.97±0.20, 29.34±0.20, 29.90±0.20, 30.20±0.20, 30.29±0.20, 31.11±0.20, 32.41±0.20, 33.49±0.20, 34.61±0.20, 35.60±0.20, 36.28±0.20, 37.22±0.20, 38.03±0.20, 38.14±0.20, 40.80±0.20, 42.00±0.20, 43.06±0.20, 43.75±0.20, 44.40±0.20, 45.50±0.20, 46.06±0.20, 46.19±0.20, 48.57±0.20, 49.91±0.20, 53.79±0.20, 54.34±0.20, 54.48±0.20, 55.72±0.20, and 63.04±0.20.

Further, in the X-ray powder diffraction of this crystal form, the relative intensity for typical peaks at above 2θ diffraction angles is:

| 2θ value (°) | Relative intensity (%) |
|---|---|
| 9.80 ± 0.20 | 10.05 |
| 10.57 ± 0.20 | 8.27 |
| 13.79 ± 0.20 | 4.63 |
| 14.93 ± 0.20 | 100.00 |
| 15.85 ± 0.20 | 5.03 |
| 17.63 ± 0.20 | 6.26 |
| 17.96 ± 0.20 | 4.02 |
| 18.27 ± 0.20 | 5.25 |
| 19.16 ± 0.20 | 9.56 |
| 19.39 ± 0.20 | 17.24 |
| 19.60 ± 0.20 | 8.59 |
| 19.78 ± 0.20 | 20.38 |
| 22.03 ± 0.20 | 3.25 |
| 22.95 ± 0.20 | 21.63 |
| 23.62 ± 0.20 | 1.73 |
| 24.92 ± 0.20 | 5.04 |
| 25.47 ± 0.20 | 1.74 |
| 26.82 ± 0.20 | 2.81 |
| 26.98 ± 0.20 | 7.87 |
| 27.97 ± 0.20 | 3.52 |
| 29.34 ± 0.20 | 6.48 |
| 29.90 ± 0.20 | 13.39 |
| 30.20 ± 0.20 | 93.68 |
| 30.29 ± 0.20 | 58.25 |
| 31.11 ± 0.20 | 5.96 |
| 32.41 ± 0.20 | 3.31 |
| 33.49 ± 0.20 | 0.21 |
| 34.61 ± 0.20 | 1.35 |

| 2θ value (°) | Relative intensity (%) |
|---|---|
| 35.60 ± 0.20 | 1.51 |
| 36.28 ± 0.20 | 1.95 |
| 37.22 ± 0.20 | 1.53 |
| 38.03 ± 0.20 | 32.97 |
| 38.14 ± 0.20 | 16.87 |
| 40.80 ± 0.20 | 1.96 |
| 42.00 ± 0.20 | 2.58 |
| 43.06 ± 0.20 | 5.89 |
| 43.75 ± 0.20 | 1.43 |
| 44.40 ± 0.20 | 1.67 |
| 45.50 ± 0.20 | 0.80 |
| 46.06 ± 0.20 | 28.08 |
| 46.19 ± 0.20 | 14.10 |
| 48.57 ± 0.20 | 1.03 |
| 49.91 ± 0.20 | 1.50 |
| 53.79 ± 0.20 | 1.86 |
| 54.34 ± 0.20 | 20.77 |
| 54.48 ± 0.20 | 10.88 |
| 55.72 ± 0.20 | 2.16 |
| 63.04 ± 0.20 | 0.99 |

Figure 2:
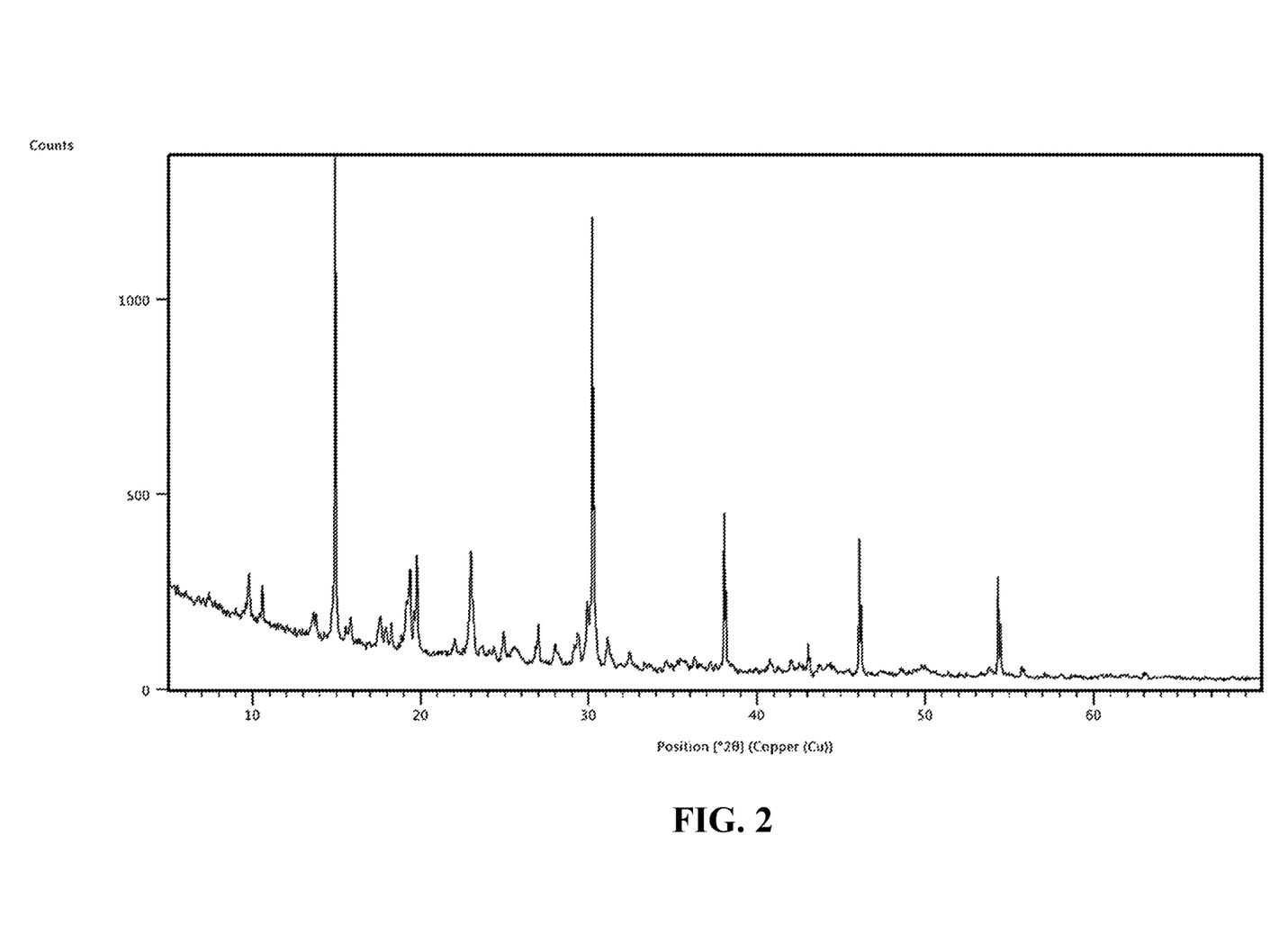
FIG. 2 is the X-ray powder diffraction pattern of crystal form B according to the present invention, using Cu-Ka irradiation.

Further, this crystal form has the X-ray powder diffraction pattern, basically as shown in FIG. 2.

The present invention also provides the uses of above compounds, crystals, or solvates thereof, or pharmaceutically acceptable salts thereof in the preparation of anti-tumor drugs.

Further, said drugs are those for the treatment of lung cancer.

Further, said lung cancer is non-small-cell lung carcinoma.

The present invention also provides a pharmaceutical composition, that is a formulation prepared by using above compounds, crystals, or solvates thereof, or pharmaceutically acceptable salts thereof as active constituents, with the addition of pharmaceutically acceptable excipients.

In the present invention, "treatment" further includes a relapse prevention or a phase prevention, as well as treating acute or chronic signs, symptoms and/or malfunctions. The treatment may be a symptomatic treatment, such as inhibiting symptoms. It can be realized in a short term, regulated in a medium term, or can be mentioned as long term therapy, such as for a maintenance therapy.

In the present invention, "pharmaceutically acceptable" means a carrier, a vector, a diluent, a adjuvant and/or a resultant salt that can be chemically or physically compatible with other constituents forming certain pharmaceutical dosage form, and physiologically compatible with acceptors.

In the present invention, said $C_1$-$C_4$ alkyl means $C_1$, $C_2$, $C_3$, and $C_4$ alkyl, i.e. straight or branch chain alkyl having 1-4 carbons, such as methyl, ethyl, propyl, isopropyl, butyl, isobutyl, tert-butyl, sec-butyl and so on.

In the present invention, "salt" means an acid salt and/or basic salt that is formed by a compound or its stereoisomer and inorganic and/or organic acid and base, and also includes amphoteric ion salts (inner salts), and further includes quaternary ammonium salts, such as alkyl ammonium salts. These salts can be directly obtained during the final separation and purification of compounds. These salts can also be obtained by suitably mixing a compound or its steroisomer with a certain amount of acid or base (such as an equivalent amount). These salts may form precipitation in the solution and can be collected by filtration method, or recovered after evaporation of solvent, or prepared by freeze drying after reaction in aqueous medium. In the present invention, said salts can be hydrochlorate, sulfate, citrate, benzenesulphonate, hydrobromate, hydrofluoride, phosphate, acetate, propionate, succinate, oxalate, malate, succinate, fumarate, maleate, tartrate or trifluoroacetate.

Experimental results show that compounds of the present invention have significant inhibitory action on lung cancer cell lines A549 and H1299, with a wide market outlook.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

The origin of reagents used in the following examples are as follows:

4-(4-morpholinemethyl)phenylboronic acid pinacol ester British Fluorochem Corporation PdCl₂dppf American Sigma-Aldrich Corporation

5-bromo-[1,2,4]triazolo[1,5-a]pyridin-2-amine American Sigma-Aldrich Corporation sodium nitrite Japanese TCI Corporation hydroiodic acid Sinopharm Chemical Reagent Co., Ltd
hydrobromic acid Japanese TCI Corporation
hydrochloric acid Chengdu Kelong Chemical Reagent Factory
cuprous cyanide Japanese TCI Corporation
acetonitrile Chengdu Kelong Chemical Reagent Factory
pyridine Sinopharm Chemical Reagent Co., Ltd Example 1 Preparation of 2-amino-5-[4-(4-morpholinylmethyl)phenyl]-[1,2,4]triazolo[1,5-a]pyridine (Compound 1)

-continued

To a 25 ml round bottom flask, was added 2 ml water and 10 ml 1,4-dioxane, and thoroughly mixed, to which were successively added 4-(4-morpholinemethyl)phenylboronic acid pinacol ester (2.85 g, 9.40 mmol), $K_2CO_3$ (1.30 g, 0.63 mmol), $PdCl_2dppf$ (0.34 g, 0.46 mmol), and 5-bromo-[1,2,4]triazolo[1,5-a]pyridin-2-amine (2 g, 9.29 mmol). The reaction was stirred at room temperature for 10 min, and the reaction solution was yellow. The reaction flask was transferred to a oil bath pan at 90° C. for refluxing, and after one hour, the reaction solution became black from yellow, and the reaction was allowed to continue for 3-5 hours, until the reaction was completed by TLC detection (developing solvent: 5% $CH_3OH/CH_2Cl_2$); after that to the flask was added 10 ml water to terminate the reaction. The reaction was transferred to a 50 ml beaker, extracted with $CH_2Cl_2$ (3×50 ml), and the organic phase was combined, to which was added 1 g anhydrous magnesium sulfate. Then the mixture was filtered, concentrated, dried, and separated by silica gel column chromatography (silica gel 10 g, eluant: 0%→2.0% $CH_3OH/CH_2Cl_2$). The product was obtained as yellow solid (2.65 g), with a yield of 92%.

The characteristic data of the structure were as follows:
m/z calcd for [M+H]$^+$, 309.195; found, 309.19.
$^1$H NMR δ 7.87 (d, J=8.1 Hz, 2H), 7.51 (d, J=8.0 Hz, 2H), 7.47 (dd, J=8.5, 7.4 Hz, 1H), 7.40 (d, J=8.7 Hz, 1H), 6.90 (d, J=7.2 Hz, 1H), 4.59 (s, 2H), 3.76 (t, J=4.4 Hz, 4H), 3.59 (s, 2H), 2.52 (s, 4H).
$^{13}$C NMR (600 MHz, CDCl$_3$): δ 53.68, 63.06, 66.97, 112.16, 112.29, 128.86, 129.22, 129.28, 131.61, 139.84, 152.03, 164.84.

Example 2 Preparation of 2-iodo-5-[4-(4-morpholinylmethyl)phenyl]-[1,2,4]triazolo[1,5-a]pyridine (Compound 2)

To a 25 ml round bottom flask, were added 2-amine-5-[4-(4-morpholinylmethyl)phenyl]-[1,2,4]triazolo[1,5-a]pyridine 100 mg (0.32 mmol) and 8 mL acetonitrile. After the substrates were dissolved by stirring at room temperature, sodium nitrite (500 mg, 7.25 mmol) was added, and the reaction mixture was stirred for 1 min, to which was slowly dropped the mixed solution prepared by 0.5 mL 45% HI solution and 2 mL acetonitrile, and red gas was produced. After stirring at room temperature for 2 hours, the same amount of HI acetonitrile solution was further added, and the reaction was allowed to continue 2-3 h, until completion of reaction by TLC (developing solvent: 5% $CH_3OH/CH_2Cl_2$); after that to the flask was added 10 ml water to terminate the reaction. The reaction was transferred to a 50 ml beaker, adjusted to neutral with $K_2CO_3$ solution (1 g/8 mL), and the solution became yellow from black. The organic phase was extracted with $CH_2Cl_2$ (3×20 ml) and combined, to which was added 1 g anhydrous magnesium sulfate. Then the mixture was filtered, concentrated, dried, and separated by silica gel column chromatography (silica gel 10 g, eluant: 0%→1.0% $CH_3OH/CH_2Cl_2$). The product was obtained as yellowy solid (101 mg), with a yield of 75%.

The characteristic data of the structure were as follows:
m/z calcd for [M+H]$^+$, 421.0525; found, 421.0548.
$^1$H NMR (600 MHz, CDCl$_3$): δ 7.83 (d, J=8.2 Hz, 2H), 7.61 (dd, J=8.9, 1.2 Hz, 1H), 7.52 (dd, J=8.8, 7.2 Hz, 1H), 7.46 (d, J=7.9 Hz, 2H), 7.01 (dd, J=7.3, 1.2 Hz, 1H), 3.69 (s, 4H), 3.53 (s, 2H), 2.45 (s, 4H).
$^{13}$C NMR (600 MHz, CDCl$_3$): δ 53.67, 63.00, 66.95, 113.97, 114.00, 116.39, 129.06, 129.37, 130.28, 140.45, 153.04.

Example 3 Preparation of 2-cyano-5-[4-(4-morpholinylmethyl)phenyl]-[1,2,4]triazolo[1,5-a]pyridine (Compound 3)

+ HI $\xrightarrow[\text{Acetonitrile}]{\text{NaNO}_2}$

+ CuCN $\xrightarrow{\text{pyridine}}$

-continued

To a 25 ml round bottom flask, were sequentially added 40 mg CuCN (0.45 mmol), 5 mL pyridine, and 2-iodo-5-[4-(4-morpholinylmethyl)phenyl]-[1,2,4]triazolo[1,5-a]pyridine (100 mg, 0.24 mmol), and then stirred at room temperature. The solution became yellowy emulsion. The flask was transferred to a oil bath pan, and refluxed at 100° C. for 1.5 h. The reaction solution was diluted with 10 mL CH$_2$Cl$_2$, followed by treatment with 1 mol/L NH$_3$.H$_2$O (2×5 mL) and 0.5 mol/L HCl (3×10 mL), respectively. The reaction mixture was extracted with CH$_2$Cl$_2$, and the organic layers were combined, to which was added 1 g anhydrous magnesium sulfate. Then the mixture was filtered, concentrated, dried, and separated by silica gel column chromatography (silica gel 10 g, eluant: 0%→1.0% CH$_3$OH/CH$_2$Cl$_2$). The product was obtained as yellowy viscous solid (35 mg), with a yield of 46%.

The characteristic data of the structure were as follows:

m/z calcd for [M+H]$^+$, 320.1512; found, 320.1609.

$^1$H NMR (600 MHz, CDCl$_3$): δ 7.89 (d, J=7.8 Hz, 2H), 7.83 (d, J=8.9 Hz, 1H), 7.76 (dd, J=8.9, 7.2 Hz, 1H), 7.62 (d, J=8.1 Hz, 2H), 7.31 (dd, J=7.5, 1.8 Hz, 1H), 3.82 (s, 4H), 3.73 (s, 2H), 2.63 (s, 4H).

Example 4 Preparation of 2-bromo-5-[4-(4-morpholinylmethyl)phenyl]-[1,2,4]triazolo[1,5-a]pyridine (Compound 4)

-continued

To a 25 ml round bottom flask, were sequentially added 2-amine-5-[4-(4-morpholinylmethyl)phenyl]-[1,2,4]triazolo[1,5-a]pyridine (150 mg, 0.48 mmol) and 10 mL acetonitrile, stirred and dissolved in ice bath, then sodium nitrite (500 mg, 7.25 mmol) was added. after stirring for 1 minute, the mixed solution prepared by 0.5 mL 47% HBr solution and 2 mL acetonitrile was slowly dropped, and after reacted under stirring for 2-3 minutes, the reaction was completed by TLC detection (developing solvent: 5% CH$_3$OH/CH$_2$Cl$_2$). The reaction solution was transferred to a 50 ml beaker, and adjusted to neutral with K$_2$CO$_3$ solution (1 g/8 mL). The organic phase was extracted with CH$_2$Cl$_2$ (3×20 ml) and combined, to which was added 1 g anhydrous magnesium sulfate. Then the mixture was filtered, concentrated, dried, and separated by silica gel column chromatography (silica gel 10 g, eluant: 0%→3.0% CH$_3$OH/CH$_2$Cl$_2$). The product was obtained as yellowy viscous solid (165 mg), with a yield of 91%.

The characteristic data of the structure were as follows:

m/z calcd for [M+H]$^+$, 373.0664; found, 373.0599.

$^1$H NMR (600 MHz, CDCl$_3$): δ 7.89 (d, J=8.2 Hz, 2H), 7.66 (ddd, J=16.0, 8.9, 4.2 Hz, 2H), 7.53 (d, J=8.1 Hz, 2H), 7.13 (dd, J=7.1, 1.4 Hz, 1H), 3.75 (t, J=4.6 Hz, 4H), 3.60 (s, 2H), 2.52 (s, 4H).

$^{13}$C NMR (600 MHz, CDCl$_3$): δ 29.70, 53.68, 63.01, 63.97, 114.16, 114.21, 129.02, 129.37, 130.38, 130.60, 140.76, 144.66, 152.52.

Example 5 Preparation of 2-chloro-5-[4-(4-morpholinylmethyl)phenyl]-[1,2,4]triazolo[1,5-a]pyridine (Compound 5)

To a 25 ml round bottom flask, were added 2-amine-5-[4-(4-morpholinylmethyl)phenyl]-[1,2,4]triazolo[1,5-a]pyridine (250 mg, 0.80 mmol) and 8 mL acetonitrile, stirred and dissolved in ice bath, then sodium nitrite (50 mg, 0.73 mmol) was added. After stirring for 1 minute, 0.2 mL 37% HCl aqueous solution was slowly dropped, and after reacted under stirring for 10-15 minutes, white diazonium salt was produced and precipitated, and the starting material completely disappeared by TLC detection (developing solvent: 5% $CH_3OH/CH_2Cl_2$). 0.5 mL 37% HCl aqueous solution was further added to dissolve the diazonium salt, and the solution became transparent yellow brown. The flask was transferred to a oil bath pan and refluxed at 80° C. for 1.5-2 hours, till no gas formation was observed. The reaction solution was transferred to a 50 mL beaker, and diluted by addition of 5 mL water, then the solution was adjusted to neutral with saturated $Na_2CO_3$ solution. The organic phase was extracted with $CH_2Cl_2$ (3×20 ml) and combined, to which was added 1 g anhydrous magnesium sulfate. Then the mixture was filtered, concentrated, dried, and separated by silica gel column chromatography (silica gel 12 g, eluant: 0%→2% $CH_3OH/CH_2Cl_2$). The product was obtained as greenyellow solid (220 mg), with a yield of 83%.

The characteristic data of the structure were as follows:
m/z calcd for $[M+H]^+$, 329.1169; found, 329.1156.

$^1$H NMR (600 MHz, $CDCl_3$): δ 7.88 (d, J=8.1 Hz, 2H), 7.69-7.63 (m, 2H), 7.53 (d, J=8.0 Hz, 2H), 7.15 (dd, J=5.7, 2.8 Hz, 1H), 3.75 (t, J=4.4 Hz, 4H), 3.60 (s, 2H), 2.52 (s, 4H).

$^{13}$C NMR (600 MHz, $CDCl_3$): δ 29.70, 53.67, 63.00, 63.97, 114.26, 114.28, 129.00, 129.38, 130.36, 130.66, 140.85, 152.12, 156.03.

Example 6 Preparation of 2-chloro-5-[4-(4-morpholinylmethyl)phenyl]-[1,2,4]triazolo[1,5-a]pyridine (Compound 6)

To a 25 ml plastic flask, were added 2-amine-5-[4-(4-morpholinylmethyl)phenyl]-[1,2,4]triazolo[1,5-a]pyridine (100 mg, 0.32 mmol) and 5 mL acetonitrile, stirred and dissolved in ice bath, then 1 mL aqueous solution of sodium nitrite (50 mg, 0.73 mmol) was added. After stirring in ice bath for 2 minutes, 0.2 mL 40% HF aqueous solution was slowly dropped, and after reacted under stirring for 30 minutes, the reaction was stirred at room temperature for 24 h, till the products were not changed by TLC detection (developing solvent: 5% $CH_3OH/CH_2Cl_2$). The reaction solution was diluted by addition of 5 mL water, and then adjusted to neutral with saturated $K_2CO_3$ solution. The organic phase was extracted with $CH_2Cl_2$ (3×20 ml) and combined, to which was added 1 g anhydrous magnesium sulfate. Then the mixture was filtered, concentrated, dried, and separated by silica gel column chromatography (silica gel 6 g, eluant: 0%→2% $CH_3OH/CH_2Cl_2$). The product was obtained as reddish brown solid (10 mg), with a yield of 10%.

Example 7 Preparation of crystal form A of 2-amino-5-[4-(4-morpholinylmethyl)phenyl]-[1,2,4]triazolo[1,5-a]pyridine (Compound 1)

To a 25 ml round bottom flask, were added 2 ml water and 10 ml 1,4-dioxane, and thoroughly mixed, to which were successively added 4-(4-morpholinemethyl)phenylboronic acid pinacol ester (2.85 g, 9.40 mmol), K$_2$CO$_3$ (1.30 g, 0.63 mmol), PdCl$_2$dppf (0.34 g, 0.46 mmol), and 5-bromo-[1,2,4]triazolo[1,5-a]pyridin-2-amine (2 g, 9.29 mmol). The reaction was stirred at room temperature for 10 min, and the reaction solution was yellow. The reaction flask was transferred to a oil bath pan at 90° C. for refluxing, and after one hour, the reaction solution became black from yellow, and the reaction was allowed to continue for 3-5 hours, until the reaction was completed by TLC detection (developing solvent: 5% CH$_3$OH/CH$_2$Cl$_2$). After that to the flask was added 10 ml water to terminate the reaction. The reaction was transferred to a 50 ml beaker, extracted with CH$_2$Cl$_2$ (3×50 ml), and the organic phase was combined, to which was added 1 g anhydrous magnesium sulfate. Then the mixture was filtered, concentrated, dried, and separated by silica gel column chromatography (silica gel 10 g, eluant: 0%→2.0% CH$_3$OH/CH$_2$Cl$_2$). The product was obtained as yellow solid (2.65 g), with a yield of 92%.

500 mg product was weighed and added into a 20 ml ampoule, and then hot alcohol at 50° C. was slowly added to dissolve, till the product was completely dissolved under continuously shaking, and transferred to a dark closed place at room temperature for overnight. After 12 hours, colorless crystal form A of the product was obtained.

The characteristic data of the structure were as follows:
m/z calcd for [M+H]$^+$, 309.195; found, 309.19.

$^1$H NMR δ 7.87 (d, J=8.1 Hz, 2H), 7.51 (d, J=8.0 Hz, 2H), 7.47 (dd, J=8.5, 7.4 Hz, 1H), 7.40 (d, J=8.7 Hz, 1H), 6.90 (d, J=7.2 Hz, 1H), 4.59 (s, 2H), 3.76 (t, J=4.4 Hz, 4H), 3.59 (s, 2H), 2.52 (s, 4H).

$^{13}$C NMR (600 MHz, CDCl$_3$): δ 53.68, 63.06, 66.97, 112.16, 112.29, 128.86, 129.22, 129.28, 131.61, 139.84, 152.03, 164.84.

FIG. 1 is the X-ray powder diffraction pattern of crystal form A according to the present invention, using Cu-Kα irradiation, and the detailed parameters are as follows

| Pos.[2θ] | Height [cts] | d-spacing [E] | l. Int. [%] |
|---|---|---|---|
| 8.5362 | 100.53 | 10.35873 | 1.65 |
| 9.8478 | 723.36 | 8.98190 | 11.91 |
| 10.1274 | 914.54 | 8.73450 | 15.05 |
| 13.5493 | 509.39 | 6.53532 | 8.38 |
| 13.7981 | 294.99 | 6.41802 | 4.86 |
| 14.4984 | 337.61 | 6.10957 | 5.56 |
| 15.3161 | 271.56 | 5.78520 | 4.47 |
| 16.3215 | 591.89 | 5.43102 | 9.74 |
| 17.1909 | 976.62 | 5.15826 | 16.07 |
| 17.4813 | 4303.50 | 5.06901 | 70.83 |
| 17.5556 | 5608.67 | 5.04774 | 92.31 |
| 17.6433 | 6075.76 | 5.02283 | 100.00 |
| 17.7230 | 3931.56 | 5.01286 | 64.71 |
| 19.3607 | 662.83 | 4.58098 | 10.91 |
| 19.8047 | 603.84 | 4.47928 | 9.94 |
| 19.9654 | 877.86 | 4.44358 | 14.45 |
| 20.1517 | 1384.76 | 4.40291 | 22.79 |
| 20.2160 | 1414.62 | 4.39996 | 23.28 |
| 20.8613 | 1636.35 | 4.25474 | 26.93 |
| 21.0111 | 1850.72 | 4.22473 | 30.46 |
| 21.2635 | 619.84 | 4.17515 | 10.20 |
| 23.8426 | 1538.53 | 3.72904 | 25.32 |
| 23.9173 | 1532.83 | 3.72680 | 25.23 |
| 24.4307 | 912.35 | 3.64059 | 15.02 |
| 24.8600 | 215.66 | 3.57868 | 3.55 |
| 26.2303 | 674.86 | 3.39475 | 11.11 |
| 27.0601 | 270.33 | 3.29251 | 4.45 |
| 27.3680 | 546.13 | 3.25615 | 8.99 |
| 27.5474 | 1068.76 | 3.23536 | 17.59 |
| 27.6361 | 1035.44 | 3.23319 | 17.04 |
| 28.3089 | 381.40 | 3.15004 | 6.28 |
| 28.4606 | 356.49 | 3.13359 | 5.87 |
| 29.5987 | 121.25 | 3.01564 | 2.00 |
| 30.4501 | 189.45 | 2.93323 | 3.12 |
| 30.7011 | 200.25 | 2.90982 | 3.30 |
| 31.6199 | 307.53 | 2.82734 | 5.06 |
| 32.6957 | 187.81 | 2.73672 | 3.09 |
| 33.4939 | 51.43 | 2.67330 | 0.85 |
| 34.1208 | 48.52 | 2.62560 | 0.80 |
| 35.9741 | 41.96 | 2.49448 | 0.69 |
| 37.1658 | 48.77 | 2.41718 | 0.80 |
| 37.7429 | 47.89 | 2.38154 | 0.79 |
| 38.1643 | 26.81 | 2.35621 | 0.44 |
| 38.9357 | 77.97 | 2.31128 | 1.28 |
| 39.2785 | 62.37 | 2.29190 | 1.03 |
| 40.1788 | 187.37 | 2.24259 | 3.08 |
| 40.8585 | 38.92 | 2.20684 | 0.64 |
| 41.5846 | 37.89 | 2.16997 | 0.62 |
| 43.0741 | 103.33 | 2.09832 | 1.70 |
| 43.6120 | 95.17 | 2.07368 | 1.57 |
| 44.9772 | 118.85 | 2.01386 | 1.96 |
| 45.2591 | 120.70 | 2.00197 | 1.99 |
| 48.2108 | 29.03 | 1.88606 | 0.48 |
| 49.2714 | 66.94 | 1.84792 | 1.10 |
| 50.9895 | 44.12 | 1.78961 | 0.73 |
| 52.7895 | 30.81 | 1.73275 | 0.51 |
| 53.5759 | 46.44 | 1.70915 | 0.76 |

Example 8 Preparation of Crystal Form B of 2-iodo-5-[4-(4-morpholinylmethyl)phenyl]-[1,2,4]triazolo[1,5-a]pyridine (Compound 2)

To a 25 ml round bottom flask, were added 2-amine-5-[4-(4-morpholinylmethyl)phenyl]-[1,2,4]triazolo[1,5-a]pyridine 100 mg (0.32 mmol) and 8 mL acetonitrile. After the substrates were dissolved by stirring at room temperature, sodium nitrite (500 mg, 7.25 mmol) was added, and the reaction mixture was stirred for 1 min, to which was slowly dropped the mixed solution prepared by 0.5 mL 45% HI solution and 2 mL acetonitrile, and red gas was produced. After stirring at room temperature for 2 hours, the same amount of HI acetonitrile solution was further added, and the reaction was allowed to continue 2-3 h, until completion of reaction by TLC (developing solvent: 5% $CH_3OH/CH_2Cl_2$). The reaction solution was transferred to a 50 ml beaker, adjusted to neutral with $K_2CO_3$ solution (1 g/8 mL), and the solution became yellow from black. The organic phase was extracted with $CH_2Cl_2$ (3×20 ml) and combined, to which was added 1 g anhydrous magnesium sulfate. Then the mixture was filtered, concentrated, dried, and separated by silica gel column chromatography (silica gel 10 g, eluant: 0%→1.0% $CH_3OH/CH_2Cl_2$). The product was obtained as yellowy solid (101 mg), with a yield of 75%.

500 mg product was weighed and added into a 20 ml ampoule, and then hot alcohol at 50° C. was slowly added to dissolve, till the product was completely dissolved under continuously shaking, and transferred to a dark closed place at room temperature for overnight. After 12 hours, yellowy crystal form of the product was obtained.

The characteristic data of the structure were as follows:
m/z calcd for [M+H]$^+$, 421.0525; found, 421.0548.

$^1$H NMR (600 MHz, CDCl$_3$): δ 7.83 (d, J=8.2 Hz, 2H), 7.61 (dd, J=8.9, 1.2 Hz, 1H), 7.52 (dd, J=8.8, 7.2 Hz, 1H), 7.46 (d, J=7.9 Hz, 2H), 7.01 (dd, J=7.3, 1.2 Hz, 1H), 3.69 (s, 4H), 3.53 (s, 2H), 2.45 (s, 4H).

$^{13}$C NMR (600 MHz, CDCl$_3$): δ 53.67, 63.00, 66.95, 113.97, 114.00, 116.39, 129.06, 129.37, 130.28, 140.45, 153.04.

FIG. 2 is the X-ray powder diffraction pattern of crystal form B according to the present invention, using Cu-Ka irradiation, and detailed parameters are as follows:

| Pos.[2θ] | Height [cts] | d-spacing [E] | Rel. Int. [%] |
|---|---|---|---|
| 9.7956 | 123.28 | 9.02963 | 10.05 |
| 10.5742 | 101.37 | 8.36646 | 8.27 |
| 13.7851 | 56.79 | 6.42408 | 4.63 |
| 14.9269 | 1226.36 | 5.93513 | 100.00 |
| 15.8472 | 61.73 | 5.59248 | 5.03 |
| 17.6270 | 76.79 | 5.03160 | 6.26 |
| 17.9637 | 49.29 | 4.93806 | 4.02 |
| 18.2703 | 64.41 | 4.85588 | 5.25 |
| 19.1562 | 117.22 | 4.63327 | 9.56 |
| 19.3907 | 211.39 | 4.57775 | 17.24 |
| 19.5979 | 105.38 | 4.52983 | 8.59 |
| 19.7818 | 249.99 | 4.48813 | 20.38 |
| 22.0331 | 39.86 | 4.03436 | 3.25 |
| 22.9454 | 265.22 | 3.87599 | 21.63 |
| 23.6165 | 21.26 | 3.76734 | 1.73 |
| 24.9234 | 61.79 | 3.57268 | 5.04 |
| 25.4728 | 21.36 | 3.49685 | 1.74 |
| 26.8159 | 34.44 | 3.32468 | 2.81 |
| 26.9798 | 96.57 | 3.30485 | 7.87 |
| 27.9731 | 43.22 | 3.18972 | 3.52 |
| 29.3358 | 79.53 | 3.04458 | 6.48 |
| 29.8955 | 164.26 | 2.98885 | 13.39 |
| 30.2005 | 1148.90 | 2.95690 | 93.68 |
| 30.2851 | 714.34 | 2.95616 | 58.25 |
| 31.1132 | 73.04 | 2.87221 | 5.96 |
| 32.4075 | 40.62 | 2.76040 | 3.31 |
| 33.4839 | 2.63 | 2.67408 | 0.21 |
| 34.6056 | 16.58 | 2.58992 | 1.35 |
| 35.5953 | 18.46 | 2.52015 | 1.51 |
| 36.2782 | 23.91 | 2.47426 | 1.95 |
| 37.2156 | 18.76 | 2.41406 | 1.53 |
| 38.0349 | 404.27 | 2.36393 | 32.97 |
| 38.1399 | 206.86 | 2.36351 | 16.87 |
| 40.8048 | 23.98 | 2.20962 | 1.96 |
| 42.0062 | 31.61 | 2.14916 | 2.58 |
| 43.0629 | 72.29 | 2.09884 | 5.89 |
| 43.7463 | 17.48 | 2.06762 | 1.43 |
| 44.3966 | 20.51 | 2.03884 | 1.67 |
| 45.4976 | 9.82 | 1.99203 | 0.80 |
| 46.0610 | 344.41 | 1.96896 | 28.08 |
| 46.1903 | 172.96 | 1.96863 | 14.10 |
| 48.5740 | 12.63 | 1.87281 | 1.03 |
| 49.9138 | 18.35 | 1.82563 | 1.50 |
| 53.7903 | 22.78 | 1.70285 | 1.86 |
| 54.3364 | 254.66 | 1.68702 | 20.77 |
| 54.4779 | 133.45 | 1.68715 | 10.88 |
| 55.7225 | 26.54 | 1.64829 | 2.16 |
| 63.0430 | 12.13 | 1.47336 | 0.99 |

Example 9 Pharmacodynamic Test of Compounds According to the Present Invention

MTT detection method was used, and MTT is a yellow compound and a dye accepting hydrogen ions, and can be used as the respiratory chain in mitochondria of viable cells. Under the action of succinate dehydrogenase and cytochrome C, the tetrazolium ring broke to form blue formanzan crystal, and the formation amount of formanzan crystal was only directly proportional to the viable counts. The formanzan crystal formed by reduction can dissolve in dimethyl sulfoxide (DMSO), and the optical density (OD) value can be determined at 490 nm using ELISA, to reflect the viable counts.

I. Experimental Procedures

Lung cancer cell lines: A549 and H1299.

Experimental materials: lung cancer cell lines, instruments and tools for cell culture, MTT, and the compound mother liquid (10 mmol/L).

1. Specific Method (3-1) Cell lines A549 and H1299 were recovered, and when the cells were in good conditions, namely cells grew to about 80% after one passage (i.e. the logarithmic growth phase), the cells were planked (96-well plate).

(3-2) Firstly, cells were collected, and the concentration of cell suspension was adjusted with counting chamber. Cells were seeded in 96-well plate at 1000-10000 cells/well, and the detailed cell numbers in each well were dependent on the growth rate of different cells and the action time of drugs.

A549 cells were seeded at 5000 cells, while H1299 cells were also seeded at 5000 cells, 200 µl for each well (100 µl cell suspension+100 µl drug dilution at different concentration gradient). The edge wells (36) were added 200 µl culture media (for prevention of edge effect).

(3-3) After planking and adding drugs, the plate was treated at 24 h, 48 h, and 72 h, and then for coloration, each well was added 200 µl culture media containing 20 µl MTT solution (5 mg/mL). The plate was continually cultured for 1-4 hours, and the culture supernatant fluid in each well was carefully absorbed. For suspension cells, the culture supernatant fluid in each well need be centrifuged before drawing. 150 µl DMSO was added to each well, and the plate was shaken on a shaking table for 15-20 min, to allow the crystals to be completely dissolved.

(3-4) Colorimetry: The colorimetry was performed by ELISA, and the optical absorption value of each well was tested at a wavelength of 490 nm or 570 nm, and the result was recorded.

(3-5) Calculation

Inhibition ratio=(the control−the drug)/the control× 100%

$IC_{50}$ (50% inhibitory concentration) can be calculated by spass software based on the inhibitory ratio at different concentration.

II. Experimental Results

A549 cells were seeded at 5000 cells/well, and after treatment for 48 h, the results were shown in Table 1:

TABLE 1

The inhibitory effect of compounds 1-3 according to the present invention against A549 cells

| Compound | Concentration | The inhibitory ratio (%) for three parallel assays | | | The mean inhibitory ratio (%) |
|---|---|---|---|---|---|
| Compound 1 | 25 µm | 10 | 9 | 10 | 10 |
|  | 50 µm | 28 | 31 | 29 | 29 |
|  | 100 µm | 31 | 31 | 30 | 31 |
| Compound 2 | 25 µm | 26 | 25 | 30 | 27 |
|  | 40 µm | 21 | 22 | 22 | 22 |
|  | 50 µm | 23 | 23 | 27 | 24 |
| Compound 3 | 25 µm | 20 | 20 | 26 | 22 |
|  | 40 µm | 22 | 24 | 20 | 22 |
|  | 50 µm | 24 | 24 | 27 | 25 |

H1299 cells were seeded at 5000 cells/well, and after treatment for 48 h, the results were shown in Table 2:

TABLE 2

The inhibitory effect of compounds 1-3 according to the present invention against H1299 cells

| Compound | Concentration | The inhibitory ratio (%) for three parallel assays | | | The mean inhibitory ratio (%) |
|---|---|---|---|---|---|
| Compound 1 | 25 µm | 63 | 61 | 63 | 62 |
|  | 50 µm | 93 | 94 | 97 | 95 |
|  | 100 µm | 86 | 84 | 86 | 85 |
| Compound 2 | 50 µm | 32 | 31 | 29 | 31 |
|  | 80 µm | 33 | 33 | 32 | 33 |
|  | 100 µm | 32 | 29 | 32 | 31 |

TABLE 2-continued

The inhibitory effect of compounds 1-3 according to the present invention against H1299 cells

| Compound | Concentration | The inhibitory ratio (%) for three parallel assays | | | The mean inhibitory ratio (%) |
|---|---|---|---|---|---|
| Compound 3 | 50 µm | 33 | 32 | 32 | 32 |
|  | 80 µm | 32 | 32 | 32 | 32 |
|  | 100 µm | 33 | 34 | 35 | 34 |

In summary, the compounds provided in the present invention have significant inhibitory effects on tumor cells, can be used for the prevention and/or treatment of tumor-related diseases, especially lung cancer, and have wide application prospects.

The invention claimed is:

1. A compound chosen from

2. A pharmaceutical composition, comprising the compound of claim 1, or the pharmaceutically acceptable salts thereof as an active ingredient, and a pharmaceutically acceptable excipient.

* * * * *